United States Patent [19]

Warrington

[11] Patent Number: 4,755,511

[45] Date of Patent: Jul. 5, 1988

[54] TRICYCLIC PYRIDAZINONE COMPOUNDS

[75] Inventor: Brian H. Warrington, Welwyn Garden City, England

[73] Assignee: Smith Kline & French Laboratories Limited, Welwyn Garden City, England

[21] Appl. No.: 99,709

[22] Filed: Sep. 22, 1987

Related U.S. Application Data

[63] Continuation of Ser. No. 793,391, Oct. 31, 1985, abandoned.

[30] Foreign Application Priority Data

Nov. 1, 1984 [GB]  United Kingdom ............... 8427688
Nov. 1, 1984 [GB]  United Kingdom ............... 8427687

[51] Int. Cl.$^4$ ................. C07D 237/36; C07D 237/26; A61K 31/50
[52] U.S. Cl. ..................... 514/248; 544/234; 558/414; 558/423; 558/426; 560/51; 562/462; 562/493; 564/215; 564/222; 564/163; 568/328; 568/330
[58] Field of Search .................. 544/234; 514/248

[56] References Cited

U.S. PATENT DOCUMENTS

| | | | |
|---|---|---|---|
| 3,464,988 | 9/1969 | Holava et al. | 544/234 |
| 4,602,019 | 7/1986 | Sircar et al. | 544/234 |
| 4,692,447 | 9/1987 | Cignarella et al. | 544/234 |

FOREIGN PATENT DOCUMENTS

| | | | |
|---|---|---|---|
| 0124314 | 4/1984 | European Pat. Off. | 544/234 |
| 0169443 | 7/1985 | European Pat. Off. | 544/234 |
| 8601506 | 3/1986 | World Int. Prop. O. | 544/234 |

OTHER PUBLICATIONS

Mukherjee et al., *J. Ind. Chem. Soc.*, 58, pp. 1023–1024 (1981).
Yamada et al., *J. Med. Chem.*, 25, pp. 975–982 (1982).
Loriga et al., *Il Farmaco*, 34:72.
Dalton et al., *Aust. J. Chem.*, 25:625.
Cignarella et al., *Il Farmaco*, 33:866 (1978).
Holava et al., *J. Med. Chem.*, 14:262 (1971).
Curran et al., *J. Med. Chem.*, 17:273 (1974).
Cignarella et al., *Il Farmaco*, 37:133 (1982).

*Primary Examiner*—Donald G. Daus
*Assistant Examiner*—E. Bernhardt
*Attorney, Agent, or Firm*—Janice E. Williams; Stuart R. Suter; Alan D. Lourie

[57] ABSTRACT

This invention relates to tricyclic pyridazinone compounds, pharmaceutical compositions containing the compounds, and a method of stimulating cardiac activity in a mammal by administering an effective amount of the compound. A compound of the invention is 7-carboxamido-4,4a-dihydro-4a-methyl-[5H]-indeno[1,2-c]-pyridazin-3[2H]-one.

11 Claims, No Drawings

TRICYCLIC PYRIDAZINONE COMPOUNDS

This is a continuation of application Ser. No. 793,391 filed Oct. 31, 1985, now abandoned.

The present invention relates to heterocyclic compounds, and in particular to such compounds having a dihydropyridazinone or pyridazinone ring as part of a tricyclic structure, pharmaceutical compositions containing them, and a method of stimulating cardiac activity by administering them.

U.S. Pat. No. 3,464,988 is directed to 5,6- dihydro-3-hydrazinobenzo [h]cinnolines and 3-hydrazino-benzocyclohepta[5,6-c]pyridazines as compounds useful in the treatment of hypertension. As intermediates for such compounds are described the compounds of the formula :

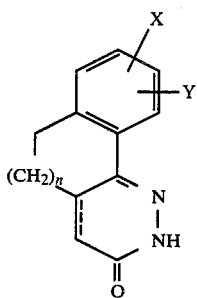

wherein n is 1 or 2, === is a single or a double bond and X and Y are selected from hydrogen, fluoro, chloro, bromo, trifluoromethyl, hydroxy, $C_{1-6}$alkyl, $C_{1-6}$alkoxy, nitro and amino. There is no suggestion of any therapeutic usefulness for such compounds. In addition the compounds wherein n is 1, === is a single or a double bond and X and Y are both hydrogen were evaluated, by Holava et al (J. Med. Chem. 1971, p 262), for analgetic, hypotensive, anti-inflammatory and central nervous system effects and reported to be "devoid of significant biological activity". The compound wherein === is a single bond n is 1 and X and Y are both hydrogen was also referred to by Dalton et al (Australian J. Chem., 1972, p 625) but only in respect of physical characteristics. Furthermore 4,4a,5,6-tetrahydro-8-methoxybenzo[h]cinnolin-3[2H]-one and the dehydro analogue were reported by Curran et al (J. Med. Chem. 1974, p 273) as not showing any hypotensive activity.

Indeno[1,2-c]pyridazin-3-one compounds of the formula:

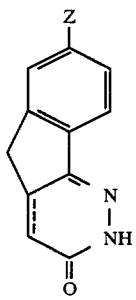

are known wherein === is a single or a double bond and Z is hydrogen (Loriga et al., Il Farmaco, 1979, 34, p 72) or fluoro (Cignarella et al., Il Farmaco, 1982, 37, p 133), or === is a single bond and Z is cyano (Loriga et al., Il Farmaco, 1979, 34, p 72 and Cignarella et al., Il Farmaco, 1978, 33, p 866), or bromo (Cignarella et al., Il Farmaco, 1978, 33, p 866). The compounds wherein Z is hydrogen, cyano and bromo are reported as having anti-inflammatory activity. The compounds wherein Z is fluorine were tested for anti-inflammatory activity but this activity was reported not to be present.

Accordingly the present invention provides a compound of the formula (I) :

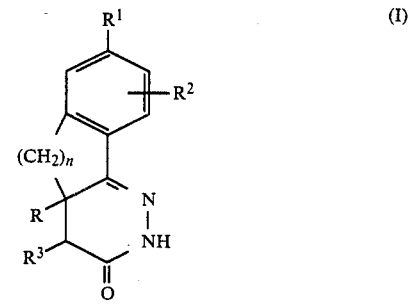

or a pharmaceutically acceptable salt thereof, wherein :
R is hydrogen or $C_{1-2}$alkyl;
$R^3$ is hydrogen;
or R and $R^3$ together form a bond;
n is one or two;
$R^1$ is hydrogen, $C_{1-6}$alkyl, $C_{1-6}$alkoxy, hydroxy, halo, cyano, amino, —$CONR^4R^5$, —$NHCONR^6R^7$, —$NHC(NCN)NHR^8$, —$NHC(NCN)R^9$, or $C_{1-6}$alkoxycarbonylamino wherein $R^4$ $R^9$ are independently hydrogen or $C^{1-6}$alkyl; and
$R^2$ is hydrogen or $C_{1-6}$alkyl;
with the proviso that when n is one and R, $R^2$ and $R^3$ are all hydrogen $R^1$ is not hydrogen, cyano or bromo or when R and $R^3$ together form a bond and n is one $R^1$ and $R^2$ are not both hydrogen : for use as a therapeutic agent.

Suitably n is one such that the compounds of the formula (I) are dihydro-indeno[1,2-c]pyridazin-3-ones or indeno[1,2-c]pyridazin-3-ones. Suitably n is two such that the compounds of the formula (I) are 4,4a,5,6-tetrahydrobenzo [h]cinnolin-3-ones or 5,6-dihydrobenzo[h]-cinnolin-3-ones.

Suitably $R^2$ is $C^{1-6}$alkyl for example methyl. Preferably $R^2$ is hydrogen.

Suitably $R^1$ is hydrogen, $C^{1-6}$alkyl for example methyl or ethyl, $C^{1-6}$ alkoxy for example methoxy or ethoxy, hydroxy or halo for example fluoro, chloro or bromo.

Suitably also $R^1$ is cyano or —$CONR^4R^5$ wherein —$NR^4R^5$ is dimethylamino, methylamino or amino.

In a further aspect $R^1$ is amino; a group —$NHCONR^6R^7$ for example ureido, N-methylureido or N,N-dimethylureido; or $C_{1-6}$alkoxycarbonylamino for example methoxycarbonyl-amino or ethoxycarbonylamino.

In addition $R^1$ is a group —$NHC(NCN)NHR^8$ or —$NHC(NCN)R^9$ for example wherein $R^8$ or $R^9$ are methyl or ethyl.

More suitably $R^1$ is hydrogen, hydroxy, methoxy, or amino.

Preferably $R^2$ is hydrogen and $R^1$ is amino.
Suitably R is hydrogen. Suitably R is methyl.
Suitably R and $R^3$ together form a bond.
Specific compounds for use in this invention are :

7-amino-4,4a-dihydro-[5H]-indeño[1,2-c]pyridazin-3[2H]-one,
7-cyano-4,4a-dihydro-4a-methyl-[5H]-indeno[1,2-c]-pyridazin-3[2H]-one,
7-carboxamido-4,4a-dihydro-4a-methyl-[5H]-indeno[1,2-c]-pyridazin-3[2H]-one,
7-amino-4,4a-dihydro-4a-methyl-[5H]-indeno[1,2-c]pyridazin-3[2H]-one,
7-bromo-4,4a-dihydro-4a-methyl-[5H]-indeno[1,2-c]pyridazin-3[2H]-one,
4,4a-dihydro-4a-methyl-[5H]-indeno[1,2-c]pyridazin-3[2H]- one,
4,4a-dihydro-7-methoxy-4a-methyl-[5H]-indeno[1,2-c]-pyridazin-3[2H]-one,
4,4a-dihydro-4a,7-dimethyl-[5H]-indeno[1,2-c]pyridazin-3-2H]-one,
4,4a-methyl-4,4a,5,6-tetrahydrobenzo[h]cinnolin-3[2H]-one,
8-methoxy-4a-methyl-4,4a,5,6-tetrahydrobenzo[h]cinnolin-[2H]-one,
4,4a-dihydro-7-ethoxy-4a-methyl-[5H]-indeno[1,2-c]-pyridazin-3[2H]-one,
7-methoxy-[5H]-indeno[1,2-c]pyridazin-3[2H]-one,
7-amino-[5H]-indeno [1,2-c]pyridazin-3[2H]-one,
5,6-dihydro-8-hydroxybenzo[h]cinnolin-3[2H]-one,
8-($N^2$-methyl-$N^3$-cyanoguanidino)-4,4a,5,6-tetrahydrobenzo-[h]cinnolin-3[2H]-one,
8-cyano-4,4a,5,6-tetrahydrobenzo[h]cinnolin-3[2H]-one,
8-carboxamido-4,4a,5,6-tetrahydrobenzo[h]cinnolin-3[2H]-one,
8-cyano-4a-methyl-4,4a,5,6-tetrahydrobenzo[h]cinnolin-3[2H]-one,
8-carboxamido-4a-methyl-4,4a,5,6-tetrahydrobenzo[h]cinnolin-3[2H]-one,
8-amino-4a-methyl-4,4a,5,6-tetrahydrobenzo[h]cinnolin-3[2H]-one,
7-($N^2$-methyl-$N^3$-cyanoguanidino)-4,4a,-dihydro-4a-methyl-5H]-indeno[1,2-c]pyridazin-3[2H]-one,
8-($N^2$-methyl-$N^3$-cyanoguanidino)-4a-methyl-4,4a,5,6-tetrahydrobenzo[h]cinnolin-3[2H]-one,
8-amino-4,4a,5,6-tetrahydrobenzo[h]cinnolin-3[2H]-one,
8-methoxy-4,4a,5,6-tetrahydrobenzo[h]cinnolin-3[2H]-one,
5,6-dihydrobenzo[h]cinnolin-3[2H]-one,
5,6-dihydro-8-methoxybenzo[h]cinnolin-3[2H]-one, and
8-amino-5,6-dihydrobenzo[h]cinnolin-3[2H]-one
and pharmaceutically acceptable salts thereof.

The compounds of the formula (I) may form pharmaceutically acceptable addition salts with either organic or inorganic acids, for example those formed with hydrochloric, hydrobromic, hydriodic, methanesulphonic, sulphuric, maleic, fumaric, succinic, acetic, oxalic, tartaric, citric and lactic acids. Pharmaceutically acceptable salts may be formed with metal ions, such as alkali metals for example sodium or potassium, or alkaline earth metals for example calcium or magnesium. The ability to form acid addition and/or metal salts will be subject to the nature of the relevant compound as will be readily understood by the skilled man.

A compound of the formula (I) or a pharmaceutically acceptable salt thereof for use in a method of therapeutic treatment of humans and other mammals is normally formulated in accordance with standard pharmaceutical practice as a pharmaceutical composition. Therefore in another aspect this invention provides a pharmaceutical composition comprising a compound of the formula (I) or a pharmaceutically acceptable salt thereof and a pharmaceutically acceptable carrier.

Compounds of the formula (I) and their pharmaceutically acceptable salts may be administered, for example, orally, parenterally, trans-dermally or rectally.

In one aspect the compositions of this invention are in sterile form.

Suitably the compounds of the formula (I) and their pharmaceutically acceptable salts may be formulated as solutions, suspensions, syrups, capsules, lozenges, reconstitutable powders, tablets and sterile forms suitable for injection or infusion. These compositions may contain conventional pharmaceutically acceptable materials such as diluents, binders, flavours, preservatives, disintegrants and colouring agents. Suitable examples of solid carriers include lactose, sucrose, talc, gelatin, agar, starch, magnesium stearate and acacia. Suitable examples of liquid carriers include polyvinylpyrrolidone, lecithin, polyethyleneglycol, arachis oil, syrup, glycerine, water, ethanol, peanut oil and olive oil.

A typical suppository formulation comprises a compound of formula (I) or a pharmaceutically acceptable salt thereof which is active when administered in this way, with a binding and/or lubricating agent for example gelatin or cocoa-butter or other low melting vegetable waxes or fats.

In another aspect, for the compounds described in the prior art referred to above the pharmaceutically acceptable carrier is preferably not ethanol, or a common organic solvent, or non-sterile water.

Preferably the composition is in unit dosage form for example a tablet or capsule. Each dosage unit contains preferably from 15 to 250 mg of a compound of the formula (I) or pharmaceutically acceptable salt thereof calculated as the free base.

This invention also provides a method of stimulating cardiac activity or treating congestive heart failure which comprises administering to a mammal, especially a human being, an effective amount of a compound of the formula (I) or a pharmaceutically acceptable salt thereof wherein :
R is hydrogen or $C_{1-2}$alkyl;
$R^3$ is hydrogen;
or R and $R^3$ together form a bond;
n is one or two
$R^1$ is hydrogen, $C_{1-6}$alkyl, $C_{1-6}$alkoxy, hydroxy, halo, amino, cyano, —$CONR^4R^5$, —$NHCONR^6R^7$, —$NHC(NCN)NHR^8$, —$NHC(NCN)R^9$, or $C_{1-6}$alkoxycarbonylamino ; wherein $R^4$ -$R^9$, are independently hydrogen or $C_{1-6}$alkyl; and $R^2$ is hydrogen or $C_{1-6}$alkyl;
and a pharmaceutical composition for stimulating cardiac activity which comprises a compound as defined immediately above and a pharmaceutically acceptable diluent or carrier.

It can be seen that this aspect of the invention encompasses some compounds of the above mentioned prior art, Loriga et al., (Il Farmaco, 1979, 34, p 72), Cignarella et al., (Il Farmaco, 1978, 33, p 866), and Cignarella et al., (Il Farmaco, 1982, 37, p 133), as such a method of treatment is not suggested therein.

The daily dosage regimen for an adult human patient is from about 15 mg to about 1500 mg of the compound of formula (I) or a pharmaceutically acceptable salt thereof calculated as the free base. The active ingredient may be administered from 1 to 6 times a day, sufficient to increase cardiac output. The compositions of the present invention have positive inotropic activity and vasodilator activity and are of use in the treatment of cardiovascular diseases which can be treated by compounds having either or both of these activities. One such disease condition is congestive heart failure.

The activity of the compounds for use in this invention as cardiac stimulants, also known as cardiotonic agents, is demonstrated by a positive inotropic effect.

The following biological test methods serve to illustrate this invention.

Cardiac Stimulant Activity — In vitro

The compounds of formula (I) and their pharmaceutically acceptable salts are tested for cardiac stimulant activity following a procedure based on that of S. C. Verma and J. H. McNeill (J. Pharm & Exp. Therapeutics, 200, 352-362 (1977)). Guinea pigs (500-700 g) of either sex are sacrificed and the hearts are quickly removed and transferred to a dissecting dish containing oxygenated bathing fluid. While in the bathing medium, the right ventricle is cut into two strips. The strips are each suspended in a 75 ml bath containing Krebs Henseleit solution at 37° C. and the bath is bubbled with 95% oxygen and 5% carbon dioxide. The ventricular strips are electrically stimulated at a frequency of 0.5 Hz, at double the threshold voltage. A resting tension of 1.0 g is applied to the strips and the tension is kept constant by readjustment during an equilibration period of 60 minutes. The bathing fluid is frequently changed during this period. When a steady base line is obtained, a compound under test is added to the bathing fluid and a cumulative concentration response curve is plotted. The compounds for use in the present invention which were tested resulted in a 50% increase in the force of contraction of the ventricular strips at concentrations in the bathing fluid of less than $10^{-4}$ molar, thus showing that they have activity as positive inotropic agents.

In the above test method the compounds of the Examples gave the following data:

| Compound of Example | $EC_{50} \times 10^{-6}$ M |
|---|---|
| 1 | 14 |
| 3 | 27 |
| 7 | 21 |
| 10 | 23 |
| 15 | 22 |
| Amrinone | 15 |

Amrinone is a marketed compound of interest that is reported to be an inotropic agent.

Cardiac Stimulant Activity — In vivo (Anaesthetised Cats)

In anaesthetised cats pretreated with a ganglion blocker (mecamylamine or pempidine) and propranolol, the compounds of the Examples cause sustained increases in left ventricular dp/dt max (this is an index of left ventricular contractility) when administered intravenously. The dose to increase left ventricular dp/dt max by 50% is given as the $ED_{50}$.

| Compound of Example | $ED_{50}$ (micromol/kg) | Relative # Duration |
|---|---|---|
| 1 | 1.8 | ** |
| 3 | 0.4 | * |
| 7 | 1.4 | ** |
| 10 | 0.2 | * |
| 15 | 1.2 | ** |
| 17 | 1.2 | ** |
| 19 | 1.6 | ** |
| Amrinone | 5.6 | * |
| X | 0.2 | *** |

Relative duration was estimated in the anaesthetised cats following the i.v. administration:
*Long: medium: *short
X represents compound of Example 1 in EP-A-150,937.

Minimal changes in blood pressure or heart rate were observed.

The compounds of this invention may be co-administered with other pharmaceutically active compounds. Conveniently the compounds of this invention and the other active compound or compounds are formulated in a pharmaceutical compositions. Examples of compounds which may be included in pharmaceutical compositions with the compounds of the formula (I) are vasodilators for example hydralazine, angiotensin converting enzyme inhibitors for example captopril, anti-anginal agents for example isosorbide nitrate, glyceryl trinitrate and pentaerythritol tetranitrate, anti-arrhythmic agents for example quinidine, procainamide and lignocaine, cardioglycosides for example digoxin and digitoxin, calcium antagonists for example verapamil and nifedipine, diuretics such as thiazides and related compounds for example benzdrofluazide, chlorothiazide, chlorothalidone, hydrochlorothiazide, and other diuretics for example frusemide and triamterene, and sedatives for example nitrazepam, flurazepam and diazepam.

In another aspect of this invention there are provided novel compounds within the formula (I) which are represented by the formula (II):

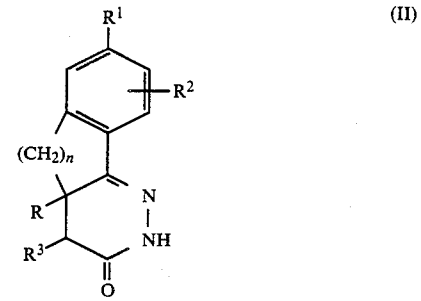

(II)

and pharmaceutically acceptable salts thereof, wherein:

R is hydrogen or $C_{1-2}$alkyl;
$R^3$ is hydrogen;
or R and $R^3$ together form a bond;
n is one or two;
$R^1$ is hydrogen, $C_{1-6}$alkyl, $C_{1-6}$alkoxy, halo, cyano, amino, hydroxy, —$CONR^4R^5$, —$NHCONR^6R^7$, $NHC(NCN)NHR^8$, —$NHC(NCN)R^9$, or $C_{1-6}$alkoxycarbonylamino wherein $R^4$ $OR^9$ are independently hydrogen or $C_{1-6}$alkyl; and
$R^2$ is hydrogen or $C_{1-6}$alkyl;
with the proviso when n is one that:
(a) $R^1$ is not hydrogen or halo when R and $R^3$ together form a bond and $R^2$ is hydrogen, or
(b) $R^1$ is not hydrogen, halo or cyano when R, $R^2$ and $R^3$ are all hydrogen,
and with the proviso when n is two that:

$R^1$ must be cyano, $CONR^4R^5$ or $-NHC(NCN)NHR^8$ when:

(i) R and $R^3$ together form a bond or
(ii) R and $R^3$ are both hydrogen.

Suitable and preferred substituents for the novel compounds of this invention are as previously described for the compounds for use as therapeutic agents.

The compounds of the formula (II) or pharmaceutically acceptable salts thereof may be prepared by a process which comprises:

(a) for compounds in which $R^3$ is H, reacting a compound of the formula (III) with hydrazine or a chemical equivalent thereof:

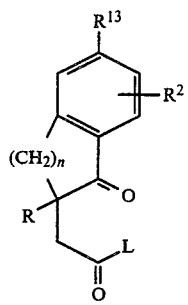

(III)

wherein R, $R^2$ and n are as hereinbefore defined, $R^{13}$ is a group $R^1$ as hereinbefore defined or a precursor thereof, and L is a leaving group, or (b) for compounds in which R and $R^3$ together form a bond, dehydrating a compound of the formula (IV):

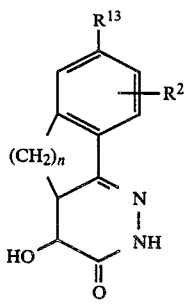

(IV)

wherein n and $R^2$ are as hereinbefore defined and $R^{13}$ is a group Rl as hereinbefore defined or $R^{13}$ is a precursor of such a group $R^1$;

and thereafter if necessary:

(i) dehydrogenating a compound wherein R and $R^3$ are both hydrogen to the corresponding compound wherein R and $R^3$ together form a bond, (ii) hydrogenating a compound wherein R and $R^3$ together form a bond to the corresponding compound wherein R and $R^3$ are both hydrogen, (iii) converting a group $R^{13}$ to a group $R^1$, (iv) forming a pharmaceutically acceptable salt.

Methods of dehydrogenation include treatment with m-nitrobenzene sulphonic acid and base or with bromine in acetic acid.

Methods of hydrogenation include those described by G. R. Brown et al., J. Chem. Soc. Commun. 1984, 1373 and particularly include treatment with zinc and acetic acid.

The reaction of a compound of formula (III) with hydrazine is conveniently performed in acidic aqueous solution, for example in aqueous acetic acid. The reaction may be performed at ambient temperature but more conveniently it may be performed at elevated temperatures for example reflux temperature.

Suitably L is amino, $C_{1-6}$alkoxy or hydroxy, preferably hydroxy or amino ($-NH_2$).

The compounds of the formula (IV) are conveniently prepared by the reaction of hydrazine or a chemical equivalent thereof with a compound of the formula (V):

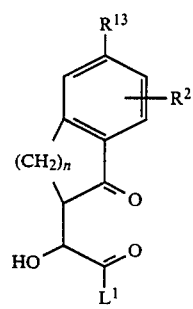

(V)

wherein $R^2$, $R^{13}$ and n are as hereinbefore defined and $L^1$ is a leaving group. This reaction may be conveniently performed in basic aqueous solution, for example at about pH 9 in the presence of ammonium ions. Conveniently the reaction is performed at an elevated temperature for example reflux.

Suitably $L^1$ is amino, $C_{1-6}$alkoxy or hydroxy, preferably hydroxy.

The dehydration of a compound of the formula (IV) may occur spontaneously thus rendering this compound an unisolated intermediate in the preparation of a compound of the formula (II) from a compound of the formula (V). In an alternative the compound of the formula (IV) may be treated with refluxing aqueous base, for example refluxing aqueous sodium carbonate, or with hydrochloric acid in acetic acid.

An example of $R^{13}$ being a precursor of a group $R^1$ is when $R^{13}$ is a nitro group. Such a group may be reduced to an amino group in conventional manner, for example via catalytic hydrogenation, for example using hydrogen gas or catalytic transfer hydrogenation. Compounds wherein $R^1$ is amino may be converted to compounds of the formula (II) wherein $R^1$ is $C_{1-6}$ alkoxycarbonylamino by conventional methods of acylation, protecting reactive groups as appropriate. Such conventional methods include using an acid halide, an acid anhydride or an activated ester. Compounds wherein $R^1$ is amino may be converted to compounds of the formula (II) wherein $R^1$ is $-NHCONHR^7$ by reacting with an appropriate isocyanate. Such a reaction is conveniently performed in an inert solvent such as dimethylformamide at an ambient or elevated temperature for example at room temperature or at a temperature up to about 100° C. Reactive groups are protected as appropriate.

In an alternative for example $R^{13}$ may be an isocyanate ($-NCO$) group which may react with an amine of formula $NHR^6R^7$, for example in an organic aprotic solvent such as dimethylformamide, at an ambient temperature. Compounds wherein $R^{13}$ is $-NCO$ may be prepared via reaction of a corresponding amino compound with a carbonylating agent, for example N,N-carbonyldi-imidazole, and need not be isolated. Such agents may be reacted in conventional manner, for example in an aprotic solvent such as dimethylformamide, at an ambient temperature or with cooling, for example at about 0° C. The reaction is performed in the presence of an organic base, for example triethylamine.

Compounds of the formula (II) wherein $R^1$ is a group —NHC(NCN)NHR$^8$ or —NHC(NCN)R$^9$ may be formed by reacting a compound of the formula (II) wherein $R^1$ is amino with a compound of the formula: $L^2$—C(NCN)NHR$^8$ or $L^2$—C(NCN)R$^9$ wherein $L^2$ is a leaving group such as $C_{1-6}$alkylthio or benzylthio, in a solvent such as pyridine at a non-extreme temperature. In an alternative compounds wherein $R^1$ is —NHC(NCN)NHR$^8$ can be prepared by reacting a compound of the formula (II) wherein $R^1$ is amino with a compound of the formula: $L^3$—C(NCN)—$L^4$ wherein $L^3$ and $L^4$ are leaving groups such as $C_{1-6}$alkoxy, phenoxy, benzyloxy or $C_{1-6}$alkylthio, conveniently in the presence of an organic base for example triethylamine; and thereafter reacting with a $C_{1-6}$alkylamine ($R^8$NH).

Compounds of the formula (II) wherein $R^1$ is carboxamido may be prepared by the hydrolysis of a corresponding compound wherein R1 is cyano.

The compounds of the formula (II) wherein $R^1$ is amino may be prepared by subjecting the corresponding compound wherein R1 is carboxamido to a Hofmann rearrangement, for example by treating with a halogen in the presence of base, for example with bromine in aqueous sodium hydroxide. An intermediate isocyanate is formed which is hydrolysed and decarboxylated to give the amino compound.

The compounds of the formula (I) may be prepared in analogous manner to that described above for the compounds of the formula (II), and reference may also be made to the aforementioned U.S. pat., Curran et al, Holava et al, Dalton et al, Loriga et al and Cignarella et al teachings.

Pharmaceutically acceptable salts of the compounds of the formulae (I) and (II) may be prepared in conventional manner, for example acid addition salts may be prepared by treating those compounds containing a basic group of the formulae (I) and (II) with the appropriate acid in a $C_{1-4}$alkanol, or they may be prepared by the use of an ion-exchange resin to form the desired salt directly from the free base or via a different acid addition salt.

The compounds of the formula (III) can be prepared by the following general routes:

(a) for compounds wherein R is hydrogen, by reaction of a compound of the formula (VI):

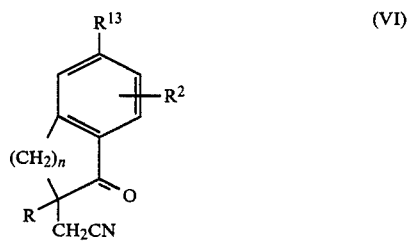

(VI)

wherein R, $R^2$, $R^{13}$ and n are as hereinbefore defined, with acid to form a compound of the formula (III) wherein L is —NH$_2$ and optionally converting L to another leaving group. Suitably concentrated sulphuric acid is used at an elevated temperature to effect the hydrolysis.

The compounds of the formula (VI) may be conveniently prepared from a compound of the formula (VII)

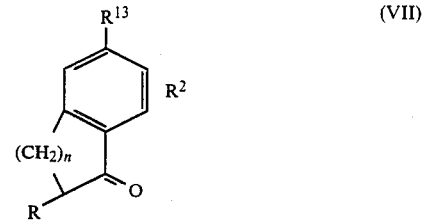

(VII)

wherein R, $R^2$, $R^{13}$ and n are as hereinbefore defined, by an acid-catalysed reaction with formaldehyde and dimethylammonium chloride and subsequent reaction with cyanide ion in a lower alkanol;

(b) for compounds wherein R is hydrogen or $C_{1-2}$alkyl, by formation of the sodium salt of a compound of the formula (VII), wherein R, $R^2$ and n are as hereinbefore defined, and $R^{13}$ is hydrogen, $C_{1-6}$alkyl, $C_{1-6}$alkoxy, halo, cyano or nitro and reaction with an alkyl bromoacetate to form a compound of the formula (III) wherein L is $C_{1-6}$alkoxy and optionally converting L to another leaving group. Suitably the sodium salt is formed by reaction with sodium hydride. Preferably the alkylbromoacetate is ethyl bromoacetate;

(c) for compounds wherein R is hydrogen or $C_{1-2}$alkyl, by bromination of a compound of the formula (VII), wherein R, $R^2$ and n are as hereinbefore defined, and $R^{13}$ is hydrogen, $C_{1-6}$alkyl, $C_{1-6}$alkoxy, halo, cyano or nitro, and reaction with the sodium derivative of a dialkyl malonate (preferably diethyl malonate) to give an intermediate diester which is hydrolysed and decarboxylated to give a compound of the formula (III) wherein L is hydroxy. Suitably the bromination is carried out using bromine or N-bromosuccinimide in a suitable solvent, preferably using bromine in acetic acid. Preferably the hydrolysis is carried out under aqueous acidic conditions;

(d) for compounds wherein R is $C_{1-2}$alkyl, by formation of the sodium salt of a compound of the formula (III) wherein R is H, $R^{13}$ is hydrogen, $C_{1-6}$alkyl, $C_{1-6}$alkoxy, halo, cyano, or nitro, and $R^2$ and L are as hereinbefore defined, and reaction with a $C_{1-2}$alkyl halide, or dialkyl sulphate. Preferably the alkylating reagent is iodomethane or dimethyl sulphate.

The compounds of the formula (V) may be conveniently prepared by reacting a compound of the formula (VII) wherein $R^2$, $R^{13}$ and n are as hereinbefore defined, and R is H, with glyoxylic acid or ester or amide thereof in aqueous medium. This reaction is generally performed in acidic medium for example using glacial acetic acid. The reaction is generally performed at an elevated temperature for example at about 80°–150° C. more suitably 100°–120° C. The compound of the formula (V) may be reacted in situ to give the compound of the formula (IV) and subsequently the compound of the formula (I) or (II).

The following Preparations, Examples and Descriptions serve to illustrate this invention.

PREPARATION 1

7-Acetamido-4,4a-dihydro-[5H]-indeno[1,2-c]pyridazin-3[2H]- one (a) Dimethylammonium chloride (8.0 g), formalin solution (5.1 ml, 37%) and concentrated hydrochloric acid (2 drops) were stirred at room temperature for 5 minutes, then added to acetic anhydride (35 ml). After 20 minutes, vigorous boiling occurred. 5-Acetamido-indanone (11.5 g) was added and the mixture stirred at 100° C. for one hour, then concentrated. The crude product was treated with acetone (100 ml) for 3 minutes then the mixture was reconcentrated. Water (150 ml) was added and unreacted ketone was extracted from the mixture into dichloromethane. The aqueous layer was separated, basified with dimethylamine and shaken with dichloromethane (100 ml). The organic layer was removed, evaporated and the gummy residue obtained was partitioned between dilute hydrochloric acid and dichloromethane. The aqueous layer was separated and concentrated to low volume to give white feathery needles (7.6 g, m.p. 182°-183° C.) of 5-acetamido-2-dimethylaminomethyl-1-indanone hydrochloride.

(b) 5-Acetamido-2-dimethylaminomethyl-1-indanone hydrochloride (6.68 g) in methanol (50 ml) and water (25 ml) was added to a stirred mixture of potassium cyanide (7.9 g), methanol (80 ml) and water (10 ml) at 60° C. Concentrated hydrochloric acid was added dropwise to give pH 7, and the mixture stirred under reflux for 30 minutes. A further portion of potassium cyanide (3.0 g) was added followed by concentrated hydrochloric acid to restore pH 7. After 20 minutes, methanol was removed under reduced pressure and, on cooling, the solution deposited 5-acetamido-2-cyanomethyl-1-indanone (5.9 g) (m.p. 182° C. resolidifies and melts sharply at 209° C.).

(c) 5-Acetamido-2-cyanomethyl-1-indanone (5.0 g) was added to stirred concentrated sulphuric acid (10.0 ml) in portions over five minutes. When half the solid had been added acetic acid (10 ml) was added to aid dissolution. The solution was heated at about 50° C. for 15 minutes, poured on to ice (100 g)/acetic anhydride (10 ml) and cooled to 0° C. Stirring was continued for one hour and the solution precipitated 5-acetamido-1-oxo-2-indanylacetamide (3.16 g, m.p. 236°-238° C.).

(d) 5-Acetamido-1-oxo-2-indanylacetamide (3.15 g) in glacial acetic acid (14 ml) and water (14 ml) was stirred under reflux with hydrazine hydrate (1.55 ml) for 30 minutes, then allowed to stand at room temperature overnight. On cooling, 7-acetamido-4,4a-dihydro-[5H]-indeno[1,2-c]pyridazin-3[2H]-one was isolated and purified by recrystallisation from glacial acetic acid-water (1.60 g, mp >300° C.); $\nu$(Nujol mull) 3300, 3230, 1697, 1656, 1635, and 1592cm$^{-1}$; $\delta$(DMSO-d$_6$) 2.09 (3H,s,COCH$_3$,) 2.60 (4H,m,4,5-H$_2$), 3.20 (1H,m,4a-H), 7.60 (3H,m,6,8,9-H), 10.13 (1H,s,N—NH, 10.76 (1H,s,CONH).

PREPARATION 2

8-Acetamido-4,4a,5,6-tetrahydrobenzo[h]cinnolin-3[2H]-one (a) Dimethylammonium chloride (2.34 g), formalin solution (1.58 g;37%) and concentrated hydrochloric acid (1 drop) was stirred at room temperature for 5 minutes then added to acetic anhydride (11.4 ml). After about 20 minutes vigorous boiling occurred. 6-Acetamido-1-tetralone (3.6 g) was then added and the mixture was stirred at 100° C. for one hour. Evaporation of the reaction mixture under reduced pressure yielded an orange solid which was treated with acetone (15 ml) for 3 minutes. The residue obtained on removal of acetone was dissolved in water (20 ml) and treated with 2N sodium hydroxide to give pH 10. The precipitated oil was extracted with dichloromethane, dried (MgSO$_4$) and evaporated to give crude 6-acetamido-2-dimethylaminomethyl-1-tetralone (5.0 g;M+ =260) which was taken up in acetone (30 ml) and treated with iodomethane (12 ml). The precipitate obtained was filtered off and washed with ether to give 6-acetamido-1-oxo-1,2,3,4-tetrahydro-2-naphthyl-trimethyl ammonium iodide (4.25 g; m.p. 168°-70°).

(b) 6-Acetamido-1-oxo-1,2,3,4-tetrahydro-2-naphthyl trimethylammonium iodide (4.25 g) in methanol (30 ml)/water (40 ml) was added to a stirred solution of potassium cyanide (1.62 g) in water (40 ml). After 3 hours the precipitate which had formed was collected and dried to give 6-acetamido-2-cyanomethyl-1-tetralone (1.7 g; m.p. 189°-90°) $\nu$(Nujol mull) 3350-3100, 2220, 1670, 1590cm$^{-1}$; m+242.

(c) In a manner similar to that described in Preparation 1(c), 6-acetamido-2-cyanomethyl-1-tetralone (1.7 g) was converted into 6-acetamido-1-oxo-1,2,3,4- tetrahydro-2-naphthylacetamide (1.55 g; m.p. 124°-5°); $\nu$(Nujol mull) 1675, 1600cm$^{-1}$.

(d) In a manner similar to that described in Preparation 1(d), 6-acetamido-1-oxo-1,2,3,4-tetrahydro-2-naphthylacetamide (1.55 g) was converted into 6-acetamido4,4a,5,6-tetrahydrobenzo[h]cinnolin-3[2H]-one (0.2 g; mp 259°); $\nu$(Nujol mull) 3330, 3215, 1655, 1610cm$^{-1}$; M+ =257.

PREPARATION 3

7-Acetamido-[5H]-indeno[1,2-c]pyridazin-3[2H]-one

A paste of 5-acetamido-1-indanone (6.3 g), glyoxylic acid monohydrate (3.13 g) and glacial acetic acid (4.0 ml) was stirred and heated on an oil bath for one hour at 105°-10°. The cooled mixture (approx 60°) was dispersed in water (13.0 ml) and treated with 0.880 ammonia solution (about 9 ml) to give pH9. The solution was filtered, treated with hydrazine hydrate (1.2 ml) and stirred under reflux for one hour. The yellow precipitate on cooling was collected by filtration, washed with water and recrystallised from dimethylformamide to give 7-acetamido-[5H]-indeno[1,2-c]pyridazin-3[2H]-one (2.8 g, m.p.>300°); $\nu$(Nujol mull) 3500, 3380-3060, 1690 and 1660 cm$^{-1}$; $\delta$(DMSO-d$_6$) 3.10 (3H,s,CH$_3$), 3.88 (2H,s,5-H$_2$), 6.85 (1H,t,4-H), 7.00 (1H,d,8-H), 7.62 (1H,s,9-H), 7.82 (1H,s,6-H), 9.90 (1H,br,NH), 12.5 (1H,br,NH).

PREPARATION 4

8-Acetamido-5,6-dihydrobenzo[h]cinnolin-3[2H]-one

In a manner similar to that described in Preparation 3, 6-acetamido-1-tetralone was treated with glyoxylic acid monohydrate and hydrazine hydrate to give 8-acetamido-5,6-dihydrobenzo[h]cinnolin-[2H]-one (mp 282°-3°). Recrystallisation from aqueous ethanol gave the monohydrate; $\nu$(Nujol mull) 3450, 3380-2500, 1680, 1660, 1625 and 1592; $\delta$(DMSO-d$_6$) 2.03 (3H,s,COCH$_3$), 2.80 (4H,s,5,6-H$_2$), 6.71 (1H,s,4-H), 7.25 (2H,m,7,9-H), 7.84 (1H,d,10-H), 9.9 (1H,s, CONH), 12.8 (1H,s,CONH).

EXAMPLE 1

7-Amino-4,4a-dihydro-[5H]-indeno[1,2-c]pyridazin-3[2H]-one

7-Acetamido-4,4a-dihydro-[5H]-indeno[1,2-c]pyridazin-3[2H]-one (1.50 g) was suspended in hydrazine hydrate (30 ml) and heated under reflux with ethanol (5 ml) for 2 hours. The solution was filtered through diatomaceous earth, allowed to cool, then extracted into chloroform. The combined organic extracts were dried over magnesium sulphate and concentrated. Recrystallisation of the crude product from n-propanol gave 7-amino-4,4a-dihydro-[5H]-indeno[1,2-c]pyridazin-3[2H]-one (0.41 g, m.p. 244°–245° C.) as a pale yellow powder; $\nu$(Nujol mull) 3400, 3320, 3220, 1652, 1635, 1600, and 1580cm$^{-1}$; $\delta$(DMSO-d$_6$) 2.50 (3H,m,4-H,5-H$_2$), 3.05 (1H,m,4a-H), 5.67 (2H,s(br),NH$_2$), 6.55 (2H,m,6,H-H), 7.27 (1H,d,9-H).

EXAMPLE 2

7-Cyano-4,4a-dihydro-4a-methyl-[5H]-indeno[1,2-c]-pyridazin-3[2H]-one

Method A

(i) A mixture of anhydrous potassium carbonate (5.45 g), paraformaldehyde (14.06 g) and p-bromopropiophen-one (100 g) in methanol (400 ml) was stirred at room temperature for 3 hours to give a clear solution. Further paraformaldehyde (20.8 g) was added and the mixture allowed to stand overnight. The mixture was then diluted with water (2.0L) and extracted with chloroform. Evaporation of the chloroform gave a clear oil containing 4-bromo-2-hydroxymethyl propiophenone, 4-bromo-2-methoxymethylpropiophenone, 1-(4-bromophenyl)prop-2-en-1-one and a small amount of unchanged starting material. This was added to concentrated sulphuric acid (300 ml) cooled in an ice-bath, stirred for 4h, allowed to stand at room temperature overnight, then poured into water (2L). Extraction with chloroform and evaporation of the extract gave a black resinous mass (112 g) which was treated with hot petrol (bp 60°–80°; 300 ml) and charcoal, allowed to cool to room temperature and filtered through diatomaceous earth. Evaporation of the filtrate gave a clear brown oil (48.12 g) which was distilled. The fraction bp 165°–70°/20 mm was collected and triturated with a little petrol (b.p. 40°–60°) to give 5-bromo-2-methyl-1-indanone (22.0 g; m.p. 55°); $\nu$(Nujol mull) 1715, 1694, 1659, 1600, 1572, 7, 828cm$^{-1}$; $\delta$(CHCl$_3$) 1.32 (3H,d,CH$_3$), 2.51–2.90 (2H,m,2,3-H), 3.37 (1H,m,3-H), 7.57 (3H,m,4,6,7-H).

(ii) 5-Bromo-2-methyl-1-indanone (2.0 g) and cuprous cyanide (4.0 g) in quinoline (50 ml) were stirred at 200° for 2 hours. The mixture was cooled, treated with chloroform (100 ml) and filtered to remove copper salts. The filtrate was then washed with 6N hydrochloric acid (3×100 ml) and evaporated to give the crude product as a brown gum. Crystallisation from ethanol-water gave 5-cyano-2-methyl-1-indanone (1.46 g, m.p. 90°–1°).

(iii) 5-Cyano-2-methyl-1-indanone (7.89 g) was added during 5 minutes to a stirred suspension of sodium hydride (1.375 g) in dry dimethylformamide (38.0 ml). After 20 minutes, when hydrogen evolution had ceased, ethyl bromoacetate (7.0 ml) was added dropwise during 5 minutes, then stirring was continued for a further 20 minutes. The mixture was poured into ice-water (200 ml) and treated with concentrated hydrochloric acid to give pH5. The orange suspension was extracted with chloroform and the extract evaporated at 100°/2.0 mm to give a brown oil containing about 30% starting indanone and about 70% ethyl (5-cyano-2-methyl-1-oxo-2-indanyl) acetate (7.28 g); $\delta$(CDCl$_3$) 1.11 (3H,t,CH$_3$CH$_2$), 1.21(3H,s CH$_3$), 2.95 (4H,m,CH$_2$CO$_2$-,3-H), 4.00 (2H,q,CH$_2$CH$_3$), 7.78 (3H,m,4,6,7-H).

(iv) Without further purification, the mixture containing about 70% ethyl (5-cyano-2-methyl-1-oxo-2-indanyl)acetate (7.0 g) was dissolved in hot 50% aqueous acetic acid (50 ml), treated with hydrazine hydrate (5.0 ml) and the mixture was stirred at reflux for 24 hours. The reaction mixture was then partially evaporated to give a syrup containing an orange solid. Ethanol was added and the solid was filtered off. Recrystallisation from aqueous ethanol gave 7-cyano-4,4a-dihydro-4a-methyl-[5H]-indeno[1,2-c]pyridazin-3[2H]-one (1.3 g m.p. 254°) $\nu$(Nujol mull) 3340, 3200, 3100, 2230, 1675, 1635, 1605cm$^{-1}$; $\delta$(DMSO-d$_6$) 1.03 (3H,s,CH$_3$), 2.62 (2H,ABq,4-H), 2.99 (2H,s,5-H), 7.8 (3H,m,6,8,9-H), 10.99 (1H,s,NH).

Method B

(i) A solution of 2-methyl-3-(3-nitrophenyl)propionic acid (105 g) in aqueous sodium hydroxide (20.4 g in 700 ml) was hydrogenated at 50psi over 10% palladium on carbon (4.0 g). After removal of the catalyst, the solution was cooled and concentrated hydrochloric acid (85 ml) was added, followed at 10° by the addition of acetic anhydride (53 ml) and sodium acetate trihydrate (76.0 g). The mixture was stirred for one hour to give 3-(3-acetamido-phenyl)-2-methylpropionic acid (107.2 g; m.p. 138.5–140.5).

(ii) A stirred mixture of 3-(3-acetamidophenyl)-2-methylpropionic acid (50.0 g) and aluminium trichloride (181 g) was heated in an oil bath (170°) for 25 minutes. The warm melt was poured with stirring on to ice (1.5kg) and the resulting mixture extracted with dichloromethane (1L). The residue from evaporation of the organic extract was heated under reflux with 2N hydrochloric acid (400 ml) for 15 minutes. The cooled solution was washed with dichloromethane (2×100 ml, 2×50 ml) and neutralised with 40% sodium hydroxide to give 24.45 g of solid product. A further 1.38 g was obtained by extraction of the filtrate and back-extraction of the dichloromethane washings. Recrystallisation from methanol or acetonitrile gave pure 5-amino-2-methyl-1-indanone (m.p. 151°–152.5°).

(iii) A solution of 5-amino-2-methyl-1-indanone (10.0 g) in fluoroboric acid (40%;28.0 ml) was treated at 0°–5° with sodium nitrite (4.7 g) in water (8.0 ml). The diazonium salt solution was added to cuprous cyanide (25.0 g) in potassium cyanide (37.5 g) in water (100 ml) at 40°. The mixture was stirred at 10° for 10 minutes, cooled and extracted with chloroform. The extract was evaporated and the residue recrystallised from aqueous ethanol to give 5-cyano-2-methyl-1-indanone(7.89 g; m.p. 90°–1°) which was converted into 7-cyano-4,4a-dihydro-[5H]-indeno[1,2-c]pyridazin-3[2H]-one by the procedures given in method A (iii, iv).

EXAMPLE 3

7-Carboxamido-4,4a-dihydro-4a-methyl-[5H]-indeno[1,2-C]-pyridazin-3[2H]-one

Finely divided 7-cyano-4,4a-dihydro-4a-methyl-[5H]-indeno[1,2-c]pyridazin-3[2H]-one (4.1 g) was sprinkled into rapidly stirred concentrated sulphuric acid (50 ml) at 40°. After all solid had dissolved the mixture was stirred for 5 minutes then poured on to ice (2500 g). The precipitated buff solid was filtered off and recrystallised from aqueous ethanol to give 7-carboxamido-4,4a-dihydro-4a- methyl-[5H]-indeno[1,2-c]pyridazin-3[2H]-one (2.7 g; m.p. 306°-7°); ν(Nujol mull) 3420, 3370, 3200, 1660cm$^{-1}$, 1638, 1609, 1600; δ(DMSO-d$_6$) 1.04 (3H,s,CH$_3$), 2.60 (2H,ABq,4-H), 2.97 (2H,s,5-H), 7.3 (2H,broad, CONH$_2$), 7.63 (1H,d,9-H), 7.85 (2H,m,6,8-H), 10.85 (1H,s,NH).

EXAMPLE 4

7-Amino-4,4a-dihydro-4a-methyl-[5H]-indeno[1,2-c]pyridazin-3[2H]-one

Bromine (0.90 ml) was added to a solution of sodium hydroxide (3.0 g) in water (20 ml) at 0°. 7-Carboxamido-4,4a-dihydro-4a-methyl-[5H]-indeno[1,2-c]pyridazinone (2.0 g) was added, then after 1 minute, a solution of sodium hydroxide (2.2 g) in water (20 ml). The mixture was heated rapidly to 80°, maintained at that temperature for 2 minutes, then cooled and acidified with concentrated hydrochloric acid. The insoluble tar was filtered off and filtrate basified to give a gummy solid containing 7-amino-4,4a-dihydro- 4a-methyl-[5H]-indeno[1,2-c]-pyridazine-3[2H]-one and ring-brominated by-products. The crude mixture was dissolved in ethanol (100 ml), treated with 2N-sodium hydroxide solution (5 ml) and hydrogenated at 40 psi in the presence of 10% palladium on carbon until no further uptake occurred. The catalyst was filtered off, and the filtrate evaporated to low bulk. Addition of water precipitated 7-amino-4,4a-dihydro-4a-methyl-[5H]-indeno[1,2-c]pyridazin-3[2H]-one; (0.5g; m.p. 222°); ν(Nujol mull) 3445, 3350, 3225, 1651, 1605, 1582 and 841cm$^{-1}$; δ(DMSO-d$_6$) 1.00 (3H,s,CH$_3$), 2.46 (2H,m,4-H), 2.75 (2H,m,5-H), 5.53 (2H,s, NH$_2$), 6.55 (2H,m,6,8-H), 7.26 (1H,d,9-H), 10.37 (1H,s,NH).

EXAMPLE 5

7-Bromo-4,4a-dihydro-4a-methyl-[5H]-indeno[1,2-c]pyridazin-3[2H]-one (i) 5-Bromo-2-methyl-1-indanone (2.0 g) was added to a suspension of sodium hydride (0.2 g) in toluene (20 ml)/dimethylformamide (2 ml) and the mixture stirred at room temperature for 3 hours. Ethyl bromoacetate (1.0 ml) was added and the mixture stirred for 4 hours. Water (5 ml) was then cautiously added, then the toluene layer was removed and evaporated. The brown oil obtained was refluxed in 2N sodium hydroxide solution (20 ml) containing a few drops of ethanol for 2 hours. The cooled reaction mixture was extracted with chloroform and the separated aqueous layer acidified with hydrochloric acid. The precipitated gum was extracted into chloroform and the extract evaporated to give crude 5-bromo-2-methyl-1-oxo-2-indanylacetic acid as a thick gum (1.0 g).

(ii) Crude 5-bromo-2-methyl-1-oxo-2-indanylacetic acid (1.0 g) was suspended in water (7.0 ml)/ethanol (7.0 ml), precipitated with hydrazine hydrate (1.0 ml) and refluxed for one hour to give a filterable yellow solid (0.45) which was recrystallised from aqueous ethanol to give 7-bromo-4,4a-dihydro-4a-methyl-[5H]-indeno[1,2-c]pyridazin-3[2H]-one (0.35 g; m.p. 242°; δ/DMSO-d$_6$) 1.03, (3H,S,CH$_3$), 2.57 (2H,m,4-H), 2.93 (2H,s,5-H), 7.50 (2H,m,6,8-H), 7.58 (1H,d,9-H), 10.81 (1H,s,NH).

EXAMPLE 6

4,4a-Dihydro-4a-methyl-[5H]-indeno[1,2-c]pyridazin-3[2H]-one (i) In a manner similar to that given in Example 2, A(iii), 2-methyl-1-indanone was converted into ethyl (2-methyl-1-oxo-2-indanyl) acetate (characterised by hydrolysis to the corresponding carboxylic acid m.p. 150°-155° C.).

(ii) In a manner similar to that given in Example 2, A(iv), ethyl (2-methyl-1-oxo-2-indanyl) acetate was converted into 4,4a-dihydro-4a-methyl-[5H]-indeno[1,2-c]-pyridazin-3[2H]-one (m.p. 197°-9°).

EXAMPLE 7

4,4a-Dihydro-7-methoxy-4a-methyl-[5H]-indeno[1,2-c]-pyridazin-3[2H]-one (i) In a manner similar to that given in Example 2, A(iii), 5-methoxy-2-methyl-1-indanone was converted into ethyl (5-methoxy-2-methyl-1-oxo-2-indanyl) acetate; δ(CDCl$_3$) 1.11 (3H,t,CH$_3$CH$_2$), 1.13 (3H,s, CH$_3$), 3.0 (4H,m,CH$_2$CO$_2$,3-H), 3.96 (3H,3,OCH$_3$), 4.15 (2H,l,CH$_2$CH$_3$), 7.5 (3H,m,4,6,7-H).

(ii) In a manner similar to that given in Example 2, A(iv), ethyl(5-methoxy-2-methyl-1-oxo-2-indanyl) acetate was converted into 4,4a-dihydro-7-methoxy-4a-methyl-[5H]-indeno[1,2-c]pyridazin-3[2H]-one (m.p. 180°-1° from industrial methylated spirits); δ(DMSO-d$_6$) 1.02 (3H,s,CH$_3$), 2.54 (2H,m,4-H), 2.90 (2H,m,5-H), 3.80 (3H,s,OCH$_3$), 6.95 (2H,m,6-H,8-H), 7.50 (1H,d,9-H), 10.61 (1H,s,NH).

EXAMPLE 8

4,4a-Dihydro-4a,7-dimethyl-[5H]-indeno[1,2-c]pyridazin-3 3[2H]-one (i) In a manner similar to that given in Example 2, A(iii), 2,5-dimethyl-1-indanone was converted into ethyl (2,5-dimethyl-1-oxo-2-indanyl) acetate.

(ii) In a manner similar to that described in Example 2, A(iv), without further purification, ethyl (2,5-dimethyl-1-oxo-2-indanyl) acetate was converted into 4,4a-dihydro-4a,7-dimethyl-[5H]-indeno[1,2-c]pyridazine-3[2H]-one (m.p. 198°-200° from EtOH) νmaximum (Nujol mull) 3210, 1665, 1615cm$^{-1}$; δ(DMSO-d$_6$) 1.02 (3H,s,7-CH$_3$), 2.34 (3H,s,4a-CH$_3$), 2,53 (2H,m,4-H), 7.48 (1H,m,9-H), 10.60 (1H,s,NH).

EXAMPLE 9

4a-Methyl-4,4a,5,6-tetrahydrobenzo[h]cinnolin-3[2H]-one (i) A mixture of 2-methyl-1-tetralone (10 g), sodium hydride (3.3 g; 50% in oil) and dry dimethylformamide (50 ml) was stirred at room temperature for 70 minutes. The solution was then cooled to 10° and ethyl bromoacetate (8.35 ml) was added during 15 minutes at 10° to 15°. After the addition, the mixture was stirred at room temperature for one hour then poured into ice-water (400 ml). Hydrochloric acid was added to pH4 and the mixture was extracted with dichloromethane. Evaporation of the extract gave 18.8 g of an oil containing ethyl (2-methyl-1-oxo-1,2,3,4-tetrahydro-2-naphthyl) acetate.

A stirred mixture of the above product and sodium hydroxide (60 ml) was heated under reflux for 30 minutes. The cooled solution was washed with dichloromethane, treated with charcoal, and acidified to give 10.1 g of a sticky solid. Recrystallisation from aqueous ethanol gave 2-methyl-1-oxo-1,2,3,4-tetrahydro-2-naphthylacetic acid (m.p. 114°–6°).

A stirred mixture of the above acid (4.0 g), dry methanol (50 ml) and concentrated sulphuric acid (0.5 ml) was heated under reflux for 2 hours.

The cold solution was poured into ice-water (400 ml), potassium bicarbonate was added to pH 7 and the mixture extracted with dichloromethane. Evaporation of the extract gave methyl (2-methyl-1-oxo-1,2,3,4-tetrahydro-2l-naphthyl) acetate (4.08 g) as an oil; $\delta(CDCl_3)$ 1.25 (3H,s,$CH_3$; 1.6–3.1 (6H,m,$CH_2CL_2$, 3,4-H), 3.6 (3H,s,$OCH_3$), 7–7.6 (3H,m,5,6,7,8-H).

(ii) A stirred mixture of methyl (2-methyl-1-oxo-1,2,3,4-tetrahydro-2- naphthyl) acetate (4.0 g), 50% aqueous acetic acid (40 ml) and hydrazine hydrate (13 ml) was heated under reflux for 64h. The mixture was cooled and the precipitated solid collected and washed with water and methanol to give the crude product (1.3 g; m.p. 179–189). Recrystallisation from acetonitrile gave pure 4a-methyl-4,4a,5,6-tetrahydrobenzo[h] cinnolin-3[2H]-one (m.p. 189°–90°).

EXAMPLE 10

8-Methoxy-4a-methyl-4,4a,5,6-tetrahydrobenzo[h]cinnolin-3[2H]-one (a) 6-methoxy-1-oxo-2,3,4,-tetrahydronaphthyl-2acetic acid (4.48 g) was added to a stirred suspension of sodium hydride (0.92 g) in dried dimethylformamide (20 ml). When effervescence had ceased iodomethane (10 ml) was added and stirring was continued for a further 2 hours at 25°. Aqueous ethanol was then added to destroy any remaining sodium hydride and the reaction mixture was filtered to remove the suspended solid. The filtrate was evaporated to dryness and the residue was refluxed in 5N sodium hydroxide solution (50 ml) for 2 hours. The mixture was cooled, shaken with chloroform, and then the aqueous layer was separated and acidified with concentrated hydrochloric acid. The precipitated oil was extracted into chloroform and passed onto a silica gel column. Elution with chloroform-ethanol (100:1) gave several fractions. The appropriate fraction was evaporated and crystallised from 1-propanol to give 6-methoxy-2-methyl-1-oxo-1,2,3,4-tetrahydronaphthyl-2-acetic acid (1.5 g; m.p. 139°–40°).

(b) In a manner similar to that given in Description 2 (iv), 6-methoxy-2-methyl-1-oxo-1,2,3,4-tetrahydronaphthyl-2-acetic acid was treated with hydrazine hydrate to give 8-methoxy-4a-methyl-4,4a,5,6-tetrahydrobenzo[h]-cinnolin-3[2H]-one (m.p. 215°; from aq. EtOH); maximum $\nu$(Nujol mull) 3320, 3200, 3090, 1675, 1615, 1595, 1500, 1240, 1040cm$^{-1}$; $\delta$(DMSO-$d_6$) 1.07 (3H,s,4a-$CH_3$), 1.6–1.9 (2H,m,5-H), 2.31 (2H,ABq,4-H), 2.7–3.0 (2H,m,6-H), 3.80 (1H,s,$OCH_3$), 6.8 (2H,m,7,9-H), 7.94 (1H,m,10-H), 10.68 (1H,s,NH).

EXAMPLE 11

4,4a-Dihydro-7-ethoxy-4a-methyl-[5H]-indeno[1,2-c]-pyridazin-3[2H]-one

Crude 5-bromo-2-methyl-1-oxo-2-indanylacetic acid (see Example 5) was refluxed in ethanol/2N sodium hydroxide (10:1) for 4 hours. Acidification of the reaction mixture gave crude 5-ethoxy-2-methyl-1-oxo-2-indanyl acetic acid as a collectable solid. Without further purification this was treated with hydrazine hydrate in a manner similar to that described in Preparation 1(d) to give 4,4a-dihydro-7-ethoxy-4a-methyl-[5H]-indeno[1,2-c]pyridazin-3[2H]-one (m.p. 211–°3° from industrial methylated spirits); $\nu$(Nujol mull) 3190, 3085, 1670, 1638, 1608, 1585, 1270 and 1051 cm$^{-1}$ $\delta$(DMSO-$d_6$) 1.01 (3H,s,$CH_3$) 1.33 (3H,t,$CH_2CH_3$), 2.51 (2H,m,4-$H_2$), 2.88(2H,m,5$H_2$), 4.07 (2H,q,$CH_2CH_3$), 6.89 (2H,m,6,8-H), 7.49 (1H,m,9-H), 10.59 (1s,NH).

EXAMPLE 12

7-Methoxy-[5H]-indeno[1,2-c]pyridazin-3[2H]-one

By a method similar to that described in Preparation 3, treatment of 5-methoxy-1-indanone with glyoxylic acid hydrate and hydrazine hydrate gave 7-methoxy-[5H]-indeno-[1,2-c]pyridazin-3[2H]-one (m.p. 280°–4°, from concentrated hydrochloric acid); $\nu$(Nujol mull) 3350–2200, 1680, 1610, 1580, 1259 and 1041 cm$^{-1}$; $\delta$(DMSO-$d_6$) 2.80 (4H,s,5,6-$H_2$), 3.73 (3H,s,$CH_3O$), 6.74 (1H,s,4-H) 7.00 (1H, dd,8-H), 7.29 (1H,dd,9-H), 7.55 (1H,dd,10-H), 12.86 (1H,br,NH).

EXAMPLE 13

7-Amino-[5H]-indeno[1,2-c]pyridazin-3[2H]-one hydrochloride

7-Acetamido-[5H]-indeno[1,2-c]pyridazin-3[2H]-one (2.0 g) in 6N hydrochloric acid (20 ml) was stirred at reflux for 3 hours. Further water (150 ml) was then added to give a clear, hot solution which was then treated with charcoal and filtered through diatomaceous earth. Concentration of the filtrate gave a buff precipitate of 7-amino-[5H]-indeno[1,2-c]pyridazin-3[2H]-one hydrochloride (1.3 g) which was collected and recrystallised from water (1.1 g, m.p. >300°); $\nu$(Nujol mull) 3200–2000, and 1696 cm$^{-1}$; $\delta$(DMSO-$d_6$) 3.92 (2H,3,5-$H_2$), 6.90 (1H,m,6-H), 7.21 (1H,m,8-H), 7.30 (1H,s,4-H), 7.71 (1H,d,9-H).

EXAMPLE 14

5,6-Dihydro-8-hydroxybenzo[h]cinnolin-3[2H]-one

In a manner similar to that given in Preparation 3, 6-hydroxy-1-tetralone was treated with glyoxylic acid monohydrate and hydrazine hydrate to give 5,6-dihydro-8-hydroxybenzo[h]cinnolin-3[2H]-one (m.p. 300°, from dimethylformamide/ethanol); $\nu$(Nujol mull) 3400–2000, 1652, 1594, and 1582cm$^{-1}$; $\delta$(DMSO-$d_6$) 2.77 (4H,s,5,6-$H_2$), 6.65 (2H,m, 4,7-H), 6.74 (1H,m,9-H), 7.73 (1H,d,10-H), 9.93 (1H,d(br),OH), 12.7 (1H,d(br)NH).

EXAMPLE 15

8-($N^2$-Methyl-$N^3$-cyanoguanidino)-4,4a,5,6-tetrahydrobenzo-[h]cinnolin-3[2H]-one (i) A mixture of 8-amino-4,4a,5,6-tetrahydrobenzo[h]-cinnolin-3[2H]-one (1.55 g) and dimethyl cyanodithioimino-carbonate (2.11 g) in dry pyridine (40 ml) was heated under reflux for 3 hours. The precipitated product was collected (1.75 g) and recrystallised from DMF/ethanol to give 8-(N-cyano-S-methylisothioureido)-4,4a,5,6-tetrahydrobenzo[h]cinnolin-3[2H]-one (1.05 g; m.p. 290°–300° (d)). $\nu$(Nujol mull) 3310, 3200, 3110, 2180, 1705, 1620, 1600 and 1530; $\delta$(DMSO-$d_6$) 1.3–1.8 (1H,m,5-H), 1.9–2.9 (6H,m,4-$H_2$,4a-H,5-H,6-$H_2$) 2.71 (3H,s,$CH_3$), 7.36 (2H,m,7,9-H), 10.10 (1H,s,NH), 10.79 (1H,s,NHCO).

(ii) A mixture of 8-(N-cyano-S-methylisothioureido)-4,4a,5,6-tetrahydrobenzo[h]cinnolin-3[2H]-one (1.0 g) and a solution of methylamine in ethanol (33%; 100 ml) was heated under reflux for 3 hours. The precipitated solid was collected and recrystallised from DMF/ethanol to give 8-($N^2$-methyl-$N^3$-cyanoguanidino)-4,4a,5,6-tetrahydrobenzo-[h]cinnolin-3[2H]-one (0.6 g; m.p. 289°). ν(Nujol mull) 3550, 3305, 3220, 3140, 2165, 1680, 1572 and 1560cm$^{-1}$; δ(DMSO-d$_6$) 1.2-1.8 (1H,m,5-H), 1.9-2.9 (6H,m,4-H$_2$,4a-H,5-H,6-H$_2$) 2.81 (3H,m,CH$_3$), 7.2 (3H,m,7,9-H), 7.94 (1H,m,10-H), 8.94 (1H,m,NH), 10.73 (1H,s,NHCO).

EXAMPLE 16

8-Cyano-4,4a,5,6-tetrahydrobenzo[h]cinnolin-3[2H]-one (i) 6-Acetamido-1-oxo-1,2,3,4-tetrahydronaphthyl-2-acetamide (17.0 g) in 10% sulphuric acid (300 ml ) was heated under reflux for 3 hours to give a solution of 6-amino-1-oxo-1,2,3,4-tetrahydro-2-naphthyl acetic acid. To the above solution was added dropwise, at 0°-5° C., a solution of sodium nitrite (5.0 g) in water (20 ml ). The resulting mixture was added to a solution of cuprous cyanide (15.0 g) and potassium cyanide (25.0 g) in water (150 ml ) at 40°. When effervescence had ceased the reaction mixture was extracted with chloroform containing about 20% methanol. The filtered extract on evaporation gave crude 6-cyano-1-oxo-1,2,3,4-tetrahydro-2-naphthyl acetic acid which was purified by extraction with saturated sodium hydrogen carbonate solution and reprecipitation from the extract with hydrochloric acid (9.1 g, m.p. 205°-210°); ν(Nujol mull) 2220, 1700, 1660, 950, and 840cm$^{-1}$.

(ii) A solution of 6-cyano-1-oxo-1,2,3,4-tetrahydro-2-naphthyl acetic acid (5.0 g) in 50% hot aqueous acetic acid was treated with hydrazine hydrate (1.0 ml ) and heated under reflux for 2 hours. The precipitated solid was filtered off and washed with water to give 8-cyano-4,4a,5,6-tetrahydrobenzo[h]cinnolin-3[2H]-one (1.2 g; m.p. 292°-5°); ν(Nujol mull) 3500, 3225, 2225, 1685, 1615, and 1586; δ(DMSO-d$_6$) 1.55 (1H,m,5-H), 2.14 (1H,m,5-H) 2.40 (2H,m,4-H), 2.78 (3H,m,4a,6-H), 7.65 (lH,m,9-H), 7.71 (lH, s, 7-H), 8.12 (1H,d,10-H), 11.04 (1H,s,NH).

EXAMPLE 17

8-Carboxamido-4,4a,5,6-tetrahydrobenzo[h]cinnolin-3[2H]-one

8-Cyano-4,4a,5,6-tetrahydrobenzo[h]cinnolin-3[2H]-one (0.6g) was added to stirred concentrated sulphuric acid at 70° . After stirring for 10 minutes at this temperature the reaction mixture was poured onto ice and the precipitated solid was filtered off. Recrystallisation from dilute acetic acid gave 8-carboxamido-4,4a,5,6-tetrahydrobenzo[h]cinnolin-3[2H]one (0.34 g, m.p. >300°). ν(Nujol mull) 3600, 3420, 3370, 3200, 1701, 1673, 1652, 1600 and 1556 cm —; δ(DMSO-d$_6$) 1.53 (1H,5-H),2.12 (1H,m,5-H) 2.22 (1H,m,4-H), 2.48 (1H,m,4-H), 2.85 (3H,m,4a,6-H), 7.21 (1H, b, NH$_2$), 7.71 (2H,m,7,9-H), 7.83 (1H,b,NH$_2$), 8.01 (1H,d,10-H).

EXAMPLE 18

8-Cyano-4a-methyl-4,4a,5,6-tetrahydrobenzo[h]cinnolin-3[2H]-one (i) 6-Cyano-1-oxo-1,2,3,4-tetrahydro-2-naphthyl acetic acid (8.0 g) was added to a stirred suspension of sodium hydride (1.8 g) in dried dimethylformamide (100 ml) at 20-30°. When effervescence has ceased, iodomethane (20 ml) was added and stirring continued for a further 2 hours at 20-30°. Water was cautiously added dropwise to the cooled reaction mixture to destroy the excess of sodium hydride. Then the reaction mixture was partitioned between water (200 ml) and dichloromethane (300 ml). The organic layer was removed, evaporated at 100° /5 mm, and the residue passed on to a silica gel column in dichloromethane. Elution with dichloromethane containing an increasing proportion of ethanol gave several fractions. The appropriate fraction was evaporated and the residue triturated with 40°-60° petroleum containing a little ether to give methyl 6-cyano-2-methyl-1-oxo-1,2,3,4-tetrahydro-2-naphthylacetate (4.0 g; m.p. 117°); ν(Nujol mull) 2220, 1738, 1660 and 1210cm$^{-1}$; δ(DMSO-d$_6$) 1.18 (3H,s,2-CH$_3$), 1.94 (1H,m,3-H) 2.31 (1H,m,3-H), 2.53 (1H,m,-CH$_2$-), 2.84 (1H,m,-CH$_2$-), 3.01 (2H, m, 4-H), 3.54 (3H,s,CH$_3$), 7.77 (1H,m,7-H), 7.86 (1H,m,5-H), 7.99 (1H,m,8-H).

(ii) A suspension of methyl 6-cyano-2-methyl-1-oxo-1,2,3,4-tetrahydro-2-naphthylacetate (4.0 g) in 2N hydrochloric acid (100 ml) and glacial acetic acid (20 ml) was stirred under reflux for 3 hours. The reaction mixture was evaporated to low bulk then extracted with chloroform. Back extraction of the chloroform extract with sodium hydrogen carbonate solution and acidification with hydrochloric acid of the separated aqueous layer game a fluffy precipitate of 6-cyano-1-oxo-1,2,3,4-tetrahydro-2-naphthyl acetic acid which was collected and washed with water (3.53 g, m.p. 168°); ν(Nujol mull) 2220, 1695, 1660 and 840 cm$^{-1}$; δ(DMSO-d$_6$) 1.18 (3H,s,2-CH$_3$), 1.91 (1H,m,3-H) 2.39 (2H,m,3-H,-CH$_2$-), 2.80 (1H,d,-CH$_2$-), 3.05 (2H,m,4-H), 7.76 (1H, d, 7-H), 7.85 (1H,s,5-H), 7.99 (1H,m,8-H).

(iii) A mixture of 6-cyano-2-methyl-1-oxo-1,2,3,4-tetrahydro-2-naphthyl acetic acid (3.5 g), hydrazine hydrate (20 ml), acetic acid (20 ml) and water (40 ml) was stirred under reflux for 4 hours. The reaction mixture was cooled and the precipitated solid filtered off. Recrystallisation from DMF/ethanol gave 8-cyano-4a-methyl-4,4a,5,6-tetrahydrobenzo[h]cinnolin-3[2H]-one (2.5 g; m.p.>300°); ν(Nujol mull) 3315, 3210, 2214, 1675, 1635, 1615, 1590 and 844 cm$^{-1}$; δ(DMSO-d$_6$) 1.06, (3H,s,CH$_3$), 1.80 (2H,m,5-H) 2.40 (2H,m,4-H), 2.92 (2H,m,6-H), 7.61 (1H,m,9-H), 7.70 (1H, s, 7-H), 8.13 (1H,d,10-H), 11.05 (1H,s,NH).

EXAMPLE 19

8-Carboxamido-4a-methyl-4,4a,5,6-tetrahydrobenzo[h]cinnolin-3[2H]-one

8-Cyano-4a-methyl-4,4a,5,6-tetrahydrobenzo[h]cinnolin-3[2H]-one (2.5 g) was dissolved in concentrated sulphuric acid (50 ml) at 40° C. then heated at 70° for 10 minutes. Without cooling the solution was poured onto ice and the precipitated solid (2.35 g) collected. Recrystallisation from ethanol gave pure 8-carboxamido-4a-methyl-4,4a,5,6-tetrahydrobenzo[h]cinnolin-3[2H]-one, m.p. 267-8°; ν(Nujol mull) 3630, 3400, 3200, 1708, 1675, 1658, and 1618 cm$^{-1}$; δ(DMSO-d$_6$) 1.07, (3H,s,CH$_3$), 1.81 (2H,m,5-H) 2.28 (1H,d,4-H), 2.48 (1H,d,4-H), 2.83 (1H,m,6-H), 3.02 (1H,m,6-H), 7.22 (1H, broad, NH$_2$), 7.71 (2H,m,7,9-H), 7.83 (1H,broad,NH$_2$), 8.05 (1H,d,10-H), 10.92 (1H,s,NH).

EXAMPLE 20

8-Amino-4a-methyl-4,4a,5,6-tetrahydrobenzo[h]cinnolin-3[2H]-one

In a manner similar to that described in Example 4, 8-carboxamido-4a-methyl-4,4a,5,6-tetrahydrobenzo[h]cinnolin-3[2H]-one (2.0 g) afforded 8-amino-4a-methyl-4,4a,5 6-tetrahydrobenzo[h]cinnolin-3[2H]-one (0.83 g;

m.p. 266–8° (water)); ν(KBr disc) 3450, 3341, 3230, 1657, 1645, 1615, 1585 and 835 cm$^{-1}$; δ(DMSO-d$_6$) 1.01, (3H,s,CH$_3$), 1.70 (2H,m,5-H) 2.24 (2H,m,4-H), 2.56 (1H,m,6-H), 2.84 (1H,m,6-H), 5.32 (2H,s,NH$_2$), 6.32 (1H,s,7-H), 6.44 (1H,m,9-H), 7.69 (1H,d,10-H), 10.46 (1H,s,NH).

EXAMPLE 21

7-(N$^2$-Methyl-N$^3$-cyanoguanidino)-4,4a,-dihydro-4a-methyl-[5H]-indeno[1,2-c]pyridazin-3[2H]-one (i) A mixture of 7-amino-4,4a,-dihydro-4a-methyl-[5H]-indeno[1,2-c]pyridazin-3[2H]-one (0.78 g), dimethyl cyanodithioiminocarbonate (1.02 g) in dry pyridine (20 ml) were stirred under reflux for 3 hours. The reaction mixture was evaporated to dryness, azeotroped several times with water and the residue triturated with acetone to give 7-(N-cyano-S-methylisothioureido)-4,4a,-dihydro-4a-methyl-[5H]-indeno[1,2-c]pyridazin-3[2H]-one (0.28 g) as a solid, m.p. 240° (d).

(ii) 7-(N-Cyano-S-methylisothioureido)-4,4a,-dihydro-4a-methyl-[5H]-indeno[1,2-c]pyridazin-3[2H]-one (0.3 g) and a solution of methylamine in ethanol (30%; 50 ml) were stirred under reflux for 4 hours. The reaction mixture was evaporated and the residue recrystallised from acetone:water:acetonitrile (2:1:2) to give 7-(N$^2$-methyl-N$^3$-cyanoguanidino)-4,4a,-dihydro-4a-methyl-[5H]-indeno[1,2-c]pyridazin-3[2H]-one (0.25 g, m.p. 210° (d)); δ(DMSO-d$_6$) 1.04, (3H,s,4a,CH$_3$), 2.55 (2H,m,4-H) 2.84 (3H,s,N-CH$_3$), 2.90 (2H,s,5-H), 7.26 (2H,m,NH,8-H), 7.35 (1H,m,6-H), 7.54 (1H,d,9-H), 8.93 (1H,s,NH), 10.69 (1H,s,CONH).

EXAMPLE 22

8-(N$^2$-Methyl-N$^3$-cyanoguanidino)-4a-methyl-4,4a,5,6-tetrahydrobenzo[h]cinnolin-3[2H]-one (i) In a similar manner to that given in Example 21, 8-amino-4a-methyl-4,4a,5,6-tetrahydrobenzo[h]cinnolin-3[2H]-one (0.26 g) was treated with dimethyl cyanodithioiminocarbonate (0.3 g) to give 8-(N-cyano-S-methylisothioureido)-4a-methyl-4,4a,5,6-tetrahydrobenzo[h]cinnolin-3[2H]-one (0.19 g; m.p. 310°). ν(Nujol mull) 2190, 1660, and 715cm$^{-1}$.

(ii) In a manner similar to that described in Example 21, 8-(N-cyano-S-methylisothioureido)-4a-methyl-4,4a,5,6-tetrahydrobenzo[h]cinnolin-3[2H]-one (0.19 g) was treated with methylamine in ethanol (30%, 20 ml) to give 8-(N$^2$-methyl-N$^3$-cyanoguanidino)-4a-methyl-4,4a,5,6-tetrahydrobenzo[h]cinnolin-3[2H]-one (0.07 g; m.p. 269°). ν(Nujol mull) 3540, 3340, 3230, 2165, 1677, 1625, 1598 and 1582 cm$^{-1}$; δ(DMS-d$_6$) 1.05, (3H,s,4a-CH$_3$), 1.76 (2H,m,5-H) 2.23 (1H,d,4-H), 2.43 (1H,d,4-H), 2.73 (1H,m,6-H), 2.81 (3H, d, N-CH$_3$), 2.92 (1H,m,6-H), 7.15 (3H,m,NH,7-H,9-H), 7.93 (1H,d,10-H), 8.84 (1H,s,NH), 10.76 (1H,s,NHCO).

EXAMPLE 23

7-(3-Methylureido)-4,4a,dihydro-4a-methyl-[5H]-indeno[1,2c]pyridazin-3-[2H]-one

A mixture of 7-amino-4,4a-dihydro-4a-methyl-[5H]-indeno(1,2c)pyridazin-3[2H]-one and methyl isocyanate in dimethylformamide is heated to afford the title compound.

EXAMPLE 24

8-Ethoxycarbonylamino-4a-methyl-4,4a,5,6-tetrahydrobenzo[h]cinnolin-3[2H]-one

A mixture of 8-amino-4a-methyl-4,4a,5,6-tetrahydrobenzo[h]-cinnolin-3[2H]-one and ethyl chloroformate in toluene is heated to afford the title compound.

EXAMPLE 25

Pharmaceutical compositions for oral administration are prepared by combining the following :

|  | % w/w |  |  |
|---|---|---|---|
| 4,4a-dihydro-7-methoxy-4a-methyl-[5H]-indeno[1,2-c]-pyridazin-3[2H]-one | 0.5 | 3.0 | 7.14 |
| 2% w/w Soya lecithin in soya bean oil | 90.45 | 88.2 | 84.41 |
| Hydrogenated vegetable shortening and beeswax | 9.05 | 8.8 | 8.45 |

The formulations are then filled into individual soft gelatin capsules.

DESCRIPTION 1

8-Amino-4,4a,5,6-tetrahydrobenzo[h]cinnolin-3[2H]-one

8-Acetamido-4,4a,5,6-tetrahydrobenzo[h]cinnolin-3[2H]-one (0.7 g) was suspended in hydrazine hydrate (13 ml) and ethanol (2 ml) and heated under reflux for 2 hours. The hot solution was filtered through diatomaceous earth and the filtrate extracted with chloroform. Evaporation of the dried (MgSO$_4$) extract gave a gum which was crystallised by trituration with 1-propanol. The crude solid was fractionated by flash chromatography (CHCl$_3$ eluant) and from the appropriate fraction was obtained 8-amino-4,4a,5,6-tetrahydrobenzo[h]cinnolin-3[2H]-one (0.25 g; m.p. 290–1° from n-propanol/water)ν(Nujol mull) 3465, 3350, 3230, 1658, 1617, 1585 cm$^{-1}$; δ(DMSO-d$_6$) 1.2–1.7 (1H,m,5-H), 1.8–2.9 (6H,m,4,4a,5,6-H) 5.35 (2H,s,NH$_2$), 6.34 (1H,m,7-H), 6.46 (1H,m,9-H), 7.66 (1H,d,10-H), 10.5 (1H,s,NHCO) M+ 215.

DESCRIPTION 2

8-Methoxy-4,4a,5,6-tetrahydrobenzo[h]cinnolin-3[2H]-one (i) In a manner similar to that described in Preparation 1(a), 6-methoxy-1-tetralone (8.0 g) was converted into 2-dimethylaminomethyl-6-methoxy-1-tetralone hydrochloride (12.0 g; m.p. 170° from acetone/water); ν(Nujol mull) 3450, 3200–2200, 1665, 1602, 1258, 1237; δ(D$_2$O) 1.70–2.32 (2H,m,3-H), 3.01 (6H,3, N(CH$_3$)$_2$), 2.80–3.20 (3H,m,2,4-H), 3.20, 3.62 (2H,m,CH$_2$N), 3.89 (3H,3,OCH$_3$), 6.90 (2H,m,5,7-H), 7.88 (1H,d,8-H).

(ii) 2-Dimethylaminomethyl-6-methoxy-1-tetralone hydrochloride (11.0 g) in methanol (100 ml)/water (50 ml) was added to a stirred solution of potassium cyanide (11.0 g) in methanol (150 ml)/water (15 ml). After 3 minutes concentrated hydrochloric acid was added dropwise to pH 7, then the mixture was stirred for 30 minutes at 60°. Further potassium cyanide (5.0 g) was added and the mixture was heated on a steam-bath for 2 hours. The cooled reaction mixture was extracted with chloroform and the dried (MgSO$_4$) extract evaporated to give a brown oil which on trituration with petroleum (b.p. 40°-60°) gave crystals of 2-cyanomethyl-methoxy-6-1-tetralone (9.0 g; m.p. 90°)νmaximum (Nujol mull) 2235, 1665, 1600 cm⁻¹; δ(CDCl₃), 6.78 (2H,m,5,7-H), 6.98 (1H,d,8-H).

(iii) A mixture of 2-cyanomethyl-6-methoxy-1-tetralone (9.0 g), 5N hydrochloric acid (200 ml) and glacial acetic acid (50 ml) was stirred and refluxed for 6 hours. The reaction mixture was cooled and the precipitated solid filtered off. The crude product was dissolved in saturated sodium hydrogen carbonate solution, treated with charcoal and filtered. Addition of concentrated hydrochloric acid to the filtrate gave pure 6-methoxy-1-oxo-1,2,3,4-tetrahydronaphthyl-2-acetic acid (7.5 g; m.p. 165-6°).

(iv) A mixture of 6-methoxy-1-oxo-1,2,3,4-tetrahydronaphthyl-2-acetic acid (2.0 g), 50% aqueous acetic acid (60 ml) and hydrazine hydrate (2.0 ml) was stirred and refluxed for 2 hours. The reaction mixture was cooled and the precipitated solid filtered off and recrystallised from aqueous ethanol to give 8-methoxy-4,4a,5,6-tetrahydrobenzo[h]cinnolin-3[2H]-one (1.07 g m.p. 198°); ν(Nujol mull) 3190, 1725, 1675, 1615, 1590, 1500, 1030 cm⁻¹; δ(DMSO-d₆) 1.30, 2.30 (2H,m,6-H), 2.31 (1H,m,4a-H), 3.77 (3H,S,OCH₃), 6,8 (2H,m,7,9-H).

DESCRIPTION 3

5H]-Indeno[1,2-c]pyridazin-3[2H]-one

By a method similar to that described in Preparation 3, 1-indanone was treated with glyoxylic acid monohydrate and hydrazine hydrate to give [5H]-indeno[1,2-c]pyridazin-3[2H]-one, m.p. 295° (from glacial acetic acid); ν(Nujol mull), 3300-2000, 1660, 1618, 1565 and 738 cm⁻¹; δ-(DMSO-d₆) 3.95 (2H,s,5-H₂), 6.92 (1H,m,4-H), 7.46 (3H,m,6,7,8-H), 7.73 (1H,m,9-H).

DESCRIPTION 4

5,6-Dihydrobenzo[h]cinnolin-3[2H]-one

In a manner similar to that described in Preparation 3, 1-tetralone was treated with glyoxylic acid monohydrate and hydrazine hydrate to give 5,6-dihydrobenzo[h]cinnolin- 3[2H]-one (m.p. 260-1°; from ethanol) ν(Nujol mull) 3350-2200, 1665, 1610 and 1600 cm⁻¹; δ(DMSO-d₆) 2.88 (4H,s,5,6-H₂), 6.77 (1H,s,4-H), approx 7.3 (3H,m,7,8,9-H), 7.92 (1H,m,10-H), 12.9 (1H,br,NH).

DESCRIPTION 5

5,6-Dihydro-8-methoxybenzo[h]cinnolin-3[2H]-one

In a manner similar to that described in Preparation 3, 6-methoxy-1-tetralone was treated with glyoxylic acid monohydrate and hydrazine hydrate to give 5,6-dihydro-8-methoxybenzo[h]cinnolin-3[2H]-one (m.p. 246-8°; from aqueous ethanol); ν(Nujol mull) 3320-2200, 1667, 1601, 1270 and 1048 cm⁻¹; δ(DMSO-d₆) 2.81 (4H,m,5,6-H₂), 3.80 (3H,s,OCH₃), 6.71 (1H,s,4-H), 6.90 (2H,m,7,9-H), 7.82 (1H,m,10-H), 12.73 (1H,s,NH).

DESCRIPTION 6

8-Amino-5,6-dihydrobenzo[h]cinnolin-3[2H]-one

In a manner similar to that described in Example 13, 8-acetamido-5,6-dihydrobenzo[h]cinnolin-3[2H]-one was hydrolysed to give 8-amino-5,6-dihydrobenzo[h]cinnolin-3[2H]-one, (m.p. 290°-292°; from aqueous ethanol); ν(Nujol mull) 3300-2200, 1680,1605, 1585, 1560 and 1545 cm⁻¹; δ(DMSO-d₆) 2.80(4H,s,5,6-H₂), 6.71(1H,s,4-H), 6.8-7.0(2H,m,7,9-H), 7.80(1H,d,10-H).

What is claimed is:

1. A compound of the formula (II):

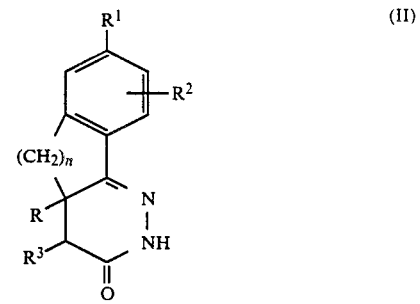

or a pharmaceutically acceptable salt thereof, wherein:
R is $C_{1-2}$ alkyl;
$R^3$ is hydrogen;
n is one or two;
$R^1$ is $-CONR^4R^5$ or $-NHC(NCN)NHR^8$ wherein $R^4$, $R^5$ and $R^8$ are independently hydrogen or $C_{1-6}$ alkyl; and $R^2$ is hydrogen or $C_{1-6}$ alkyl.

2. A compound according to claim 1 wherein $R^2$ is hydrogen.

3. A compound according to claim 1 or 2 wherein R is methyl.

4. A compound according to claim 1 which is: 7-carboxamido-4,4a-dihydro-4a-methyl-[5H]-indeno[1,2-c]-pyridazin-3[2H]-one or a pharmaceutically acceptable salt thereof.

5. A compound according to claim 1 which is: 8-carboxamino-4a-methyl-4,4a,5,6-tetrahydrobenzoh[h]cinnolin-3[2H]-one or a pharmaceutically acceptable salt thereof.

6. A compound according to claim 1 which is 7-(N²-methyl-N³-cyanoguanidine)-4,4a-dihydro-4a-methyl-[5H]-indeno[1,2-c]pyridazin-3[2H]-one or 8-(N²-methyl-N³-cyanoguanidino)-4a-methyl-4,4a,5,6-tetrahydrobenzo[h]cinnolin-3[2H]-one, or a pharmaceutically acceptable salt thereof.

7. A pharmaceutical composition for stimulating cardiac activity which comprises a cardiac stimulating effective amount of a compound of the formula (I):

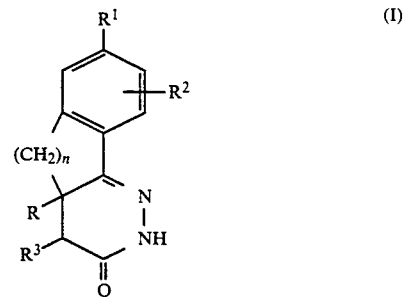

or a pharmaceutically acceptable salt thereof, wherein:
R is $C_{1-2}$alkyl;
$R^3$ is hydrogen;
or R and $R^3$ together form a bond;
n is one or two;
$R^1$ is $-CONR^4R^5$ or $-NHC(NCN)NHR^8$, wherein $R^4$, $R^5$ and $R^8$ are independently hydrogen or $C_{1-6}$alkyl; and $R^2$ is hydrogen or $C_{1-6}$alkyl;

and a pharmaceutically acceptable diluent or carrier.

8. A pharmaceutical composition for stimulating cardiac activity according to claim 7 for oral administration.

9. A pharmaceutical composition for stimulating cardiac activity according to claim 7 in unit dosage form.

10. A method for stimulating cardiac activity in a mammal comprising internally administering an effective amount of a compound of formula (I):

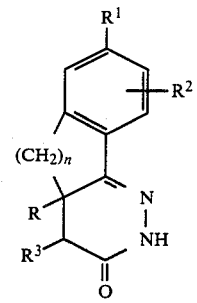

or a pharmaceutically acceptable salt thereof, wherein:
$R$ is hydrogen or $C_{1-2}$alkyl;
$R^3$ is hydrogen;
or $R$ and $R^3$ together form a bond;
$n$ is one or two;
$R^1$ is hydrogen, $C_{1-6}$alkyl, $C_{1-6}$alkoxy, hydroxy, halo, cyano, —CONR$^4$R$^5$ or —NHC(NCN)NHR$^8$, wherein R$^4$, R$^5$ and R$^8$ are independently hydrogen or $C_{1-6}$alkyl; and
$R^2$ is hydrogen or $C_{1-6}$alkyl;

11. A method according to claim 10 for stimulating cardiac activity in a mammal comprising internally administering an effective amount of 7-carboxamido-4,4a-dihydro-4a-methyl-[5H]-indeno[1,2-c]-pyridazin-3[2H]-one or a pharmaceutically acceptable salt thereof.

* * * * *